US009993506B1

(12) United States Patent
Brahm

(10) Patent No.: US 9,993,506 B1
(45) Date of Patent: Jun. 12, 2018

(54) METHODS FOR THE TREATMENT OF DEGENERATIVE DISC DISEASES BY HUMAN BIRTH TISSUE MATERIAL COMPOSITION

(71) Applicant: BioDlogics, LLC, Cordova, TN (US)

(72) Inventor: Timothy R. Brahm, Germantown, TN (US)

(73) Assignee: BioDlogics, Inc., Cordova, TN (US)

( * ) Notice: Subject to any disclaimer, the term of this patent is extended or adjusted under 35 U.S.C. 154(b) by 81 days.

(21) Appl. No.: 14/215,487

(22) Filed: Mar. 17, 2014

Related U.S. Application Data

(60) Provisional application No. 61/802,430, filed on Mar. 16, 2013.

(51) Int. Cl.
| | | |
|---|---|---|
| *A61K 35/50* | (2015.01) | |
| *A61K 35/51* | (2015.01) | |
| *A61K 35/48* | (2015.01) | |
| *A61K 9/00* | (2006.01) | |

(52) U.S. Cl.
CPC ............ *A61K 35/51* (2013.01); *A61K 9/0019* (2013.01); *A61K 35/48* (2013.01); *A61K 35/50* (2013.01)

(58) Field of Classification Search
CPC ......... A61K 35/51; A61K 35/48; A61K 35/50
See application file for complete search history.

(56) References Cited

U.S. PATENT DOCUMENTS

| | | |
|---|---|---|
| 3,409,016 A | 11/1968 | Foley |
| 5,036,056 A | 7/1991 | Kludas |
| 6,152,142 A | 11/2000 | Tseng |
| 6,326,019 B1 | 12/2001 | Tseng |
| 7,727,550 B2 | 6/2010 | Siegal et al. |
| 7,871,646 B2 | 1/2011 | Ghinelli |
| 8,071,135 B2 | 12/2011 | Liu et al. |
| 8,153,162 B2 | 4/2012 | Tseng et al. |
| 8,182,840 B2 | 5/2012 | Tseng et al. |
| 8,182,841 B2 | 5/2012 | Tseng et al. |
| 8,187,639 B2 | 5/2012 | Tseng et al. |
| 8,956,862 B2 | 2/2015 | Pal et al. |
| 2004/0057938 A1 | 3/2004 | Ghinelli |
| 2007/0021762 A1 | 1/2007 | Liu et al. |
| 2007/0031471 A1 | 2/2007 | Peyman |
| 2007/0292401 A1 | 12/2007 | Harmon et al. |
| 2011/0280838 A1* | 11/2011 | Kramer .................. A61K 35/50 424/93.3 |
| 2012/0141595 A1 | 6/2012 | Tseng et al. |
| 2013/0287741 A1 | 10/2013 | Stilwell et al. |
| 2014/0037598 A1 | 2/2014 | Jansen et al. |
| 2014/0050788 A1 | 2/2014 | Daniel et al. |
| 2014/0052247 A1 | 2/2014 | Daniel et al. |

FOREIGN PATENT DOCUMENTS

| | | |
|---|---|---|
| EP | 0285370 | 10/1988 |
| WO | WO-2006/094247 | 1/2006 |
| WO | WO-2009/052132 | 1/2009 |
| WO | WO-2012/003377 | 1/2012 |

OTHER PUBLICATIONS

Majore et al., Identification of subpopulations in mesenchymal stem cell-like cultures from human umbilical cord. Cell Communication and Signaling, vol. 7, No. 6 (Mar. 20, 2009).*
R. Ian Freshney, "Primary Culture." In: Culture of Animal Cell: A Manual of Basic Technique and Specialized Applications. (Hoboken, NJ, John Wiley & Sons, Inc., 2010), pp. 163-186.*
Richardson et al., Mesenchymal stem cells in regenerative medicine: Focus on articular cartilage and intervertebral disc regeneration. Methods, vol. 99 (Apr. 15, 2016) pp. 69-80.*
Wang et al., Mesenchymal stem cells in the Wharton's jelly of the human umbilical cord. Stem Cells, vol. 22, No. 7 (Dec. 2004) pp. 1330-1337.*
Avanzi et al., *Susceptibility of Human Placenta Derived Mesenchymal Stromal/Stem Cells to Human Herpesviruses Infection*, PLOS One, vol. 8, Issue 8, pp. 1-14, Aug. 2013.
Brooke et al., *Manufacturing of human placenta-derived mesenchymal stem cells for clinical trials*, British Journal of Haematology, 144, pp. 571-579, 2008.
Fuller et al., Stem Cells, Clinical Applications of Cryobiology, pp. 127-134, 2000.
Gavin, *Histopathology of "fresh" human aortic valve allografts*, Thorax, 28, pp. 482-487, 1973.
Kagan, *The Skin Bank*, Chapter 15, in Total Burn Care, pp. 199-208, 2012.
Parolini et al., *Concise Review: Isolation and Characterization of Cells from Human Term Placenta: Outcome of the First International Workshop on Placenta Derived Stem Cells*, Stem Cells 2008, 26, pp. 300-311, 2008.
Sabapathy et al., *Long-Term Cultured Human Term Placenta-Derived Mesenchymal Stem Cells of Maternal Origin Displays Plasticity*, Stem Cells International, vol. 2012, pp. 1-11, 2012.
Haimov-Kochman et al. "Modification of the standard trizol-based technique improves the integrity of RNA isolated from RNaserich placetal tissue", Clinical Chemistry, 2006, 52(1):159-160.

* cited by examiner

*Primary Examiner* — Kara Johnson
(74) *Attorney, Agent, or Firm* — Brinks Gilson & Lione

(57) ABSTRACT

Methods for treating degenerative disc disease by administering a human birth tissue material composition are provided. The method includes the step of administering a human birth tissue material composition onto or into at least one intervertebral disc or intervertebral space in need of treatment.

16 Claims, 3 Drawing Sheets

| | BATCH VOLUME AND ALIQUOT FILL CALCULATION | | | | | |
|---|---|---|---|---|---|---|
| A. | AMNION WEIGHT (AW) | | | | | |
| | | | | Amnion Weight (g) | (AW) _____ g | |
| B. | AMNION ALLOWABLE ALIQUOTS (AA) | | | | | |
| | (AW) _____ g / 0.03 g = | | | | (AA) _____ | |
| | Amnion Weight(g)   Minimum Amnion(g) per 1mL aliquot | | | | | |
| C. | CELL COUNT | | | | | |
| | Amniotic Fluid Volume (mL) (A) | Total Cells Counted (5 Large Squares) (B) | Average Cells / Square (C) (C = B / 5) | Dilution Factor (D) | Total Cell Density (E) (Cells/mL) (E = C x D x $10^4$) | Total Cells (TC) (TC = E x A) |
| | (A) | (B) | (C) | (D) | (E) | (TC) |
| D. | ALIQUOT CELL DENSITY (ALIQUOT = 1 mL) | | | | | |
| | (TC) _____ / (AA) _____ = | | | | (CD) _____ ml | |
| | Total Cells         Amnion Allowable Aliquot | | | | Aliquot Cell Density | |
| E. | BULK PRODUCT VOLUME (BV) | | | | | |
| | (AA) _____ = (BV) _____ | | | | | |
| F. | LOT VIAL FILL CALCULATIONS | | | | | |
| | Bulk Product Volume   (BV) | | = | | | mL |
| | Actual Vial Target 0.25 mL = | | X 0.25 = | | | mL |
| | Actual Vial Target 0.50 mL = | | X 0.50 = | | | mL |
| | Actual Vial Target 1.25 mL = | | X 1.25 = | | | mL |
| | TOTAL VIAL Target | | Total Vial Fill Volume* | | | mL |
| | * Total Vial Fill Volume Must be ≤ Bulk Product Volume | | | | | |

FIG. 2

| | SOLUTION CALCULATIONS | | |
|---|---|---|---|
| | SUSPENSION SOLUTIONS (SS) CALCULATIONS | | |
| a) | (BV) _____ mL = (SS) _____ mL<br>Bulk Product Volume (mL)     Total Suspension Solution Volume (mL) | | |
| i) | Cell Suspension Solution (CS) | | |
| | _____ (SS) / 2 = | | _____ mL (CS) |
| | Component Description | Volume Calculation | Volume Required |
| | Plasma Lyte-A Injection (pH 7.4) | (CS) x 0.91 = | _____ mL |
| | Human Albumin 25% Solution | (CS) x 0.09 = | _____ mL |
| ii) | Amnion Suspension Solution (AS) | | |
| | _____ (SS) / 2 = | | _____ mL (AS) |
| | Component Description | Volume Calculation | Volume Required |
| | Plasma Lyte-A Injection (pH 7.4) | (AS) x 0.44 = | _____ mL |
| | Human Albumin 25% Solution | (AS) x 0.36 = | _____ mL |
| | DMSO (Dimethyl Sulfoxide), USP | (AS) x 0.20 = | _____ mL |
| b) | AMNION CONTROL RATE FREEZE SOLUTION = 50 mL | | |
| | Component Description | Volume Calculation | Volume Required |
| | Plasma Lyte-A Injection (pH 7.4) | 50 ml x 0.44 = | 22 mL |
| | Human Albumin 25% Solution | 50 ml x 0.36 = | 18 mL |
| | DMSO (Dimethyl Sulfoxide), USP | 50 ml x 0.20 = | 10 mL |

FIG. 3

METHODS FOR THE TREATMENT OF DEGENERATIVE DISC DISEASES BY HUMAN BIRTH TISSUE MATERIAL COMPOSITION

CROSS-REFERENCE TO RELATED APPLICATIONS

This application claims priority to U.S. Provisional Patent Application No. 61/802,430 filed Mar. 16, 2013, the contents of which is incorporated herein in its entirety.

FIELD OF THE INVENTION

Methods for treating degenerative disc disease by administering a human birth tissue material composition are provided.

BACKGROUND OF THE INVENTION

Intervertebral discs, which lie between adjacent vertebrae in the spine, provide the vertebral column with the necessary biomechanical properties for movement and compressive strength. Each disc forms a cartilaginous joint to allow slight movement of the vertebrae and acts as a ligament to hold the vertebrae together. Intervertebral discs are composed of three tissue types, namely, the annulus fibrosis (AF), the nucleus pulposis (NP) and the end plates. The AF consists of a series of loosely connected concentric layers of collagen tissue that surround the NP and distribute pressure evenly across the disc. The NP is formed from a network of collagen fibrils that are loosely embedded in a gelatinous matrix of proteoglycan aggrecans and chondrocytes. Alteration of the biomechanical properties of intervertebral discs is suspected to be the leading cause of degenerative disc disease and of debilitating back pain. A diverse range of factors, including mechanical, biochemical, nutritional, and genetic factors, are known to contribute to the development of degenerative disc disease. Examples include: abnormal mechanical loading, genetic predisposition, and reduced cellular activity.

The treatment of pain associated with degenerative disc disease usually involves conservative treatments, such as physical therapy and medication. Surgical intervention, usually by discectomy, is reserved for those patients who fail conservative treatment. Discectomy provides relief from pain originating from the compression of neural structures by the surgical removal of disc tissue; however, such surgeries do not treat the underlying biological problem. Spinal fusion, a surgical technique used to join two or more vertebrae, is another surgical intervention option that is often performed in combination with discectomy to immobilize the affected vertebrae. Supplementary bone tissue (e.g., autologous iliac crest bone, allograft tissue, synthetic cage with bone substitute filler) is used in conjunction with the body's natural bone growth processes to fuse the vertebrae. However, autologous tissue recovery often leads to graft site morbidity. Furthermore, fusion often leads to adjacent segment disease, which may limit the duration of success of the operation. Thus, there remains a need for safe, effective methods for treating degenerative disc disease.

SUMMARY OF THE INVENTION

A method of treating degenerative disc disease in a subject is provided. The method includes the step of administering a human birth tissue material composition onto or into at least one intervertebral disc or at least one intervertebral space in need of treatment. According to one embodiment, the birth tissue material composition includes one or more components of the placental organ. According to one embodiment, the one or more of the components of the placental organ can be the placental globe, the umbilical cord, the umbilical cord blood, the chorionic membrane, the amniotic membrane, the Wharton's jelly, the amniotic fluid, and other placental gelatins, cells, or extracellular material. According to one embodiment, the human birth tissue material composition is administered via implantation of a delivery device between a first vertebral body and second vertebral body. According to one embodiment, the human birth tissue material composition is administered via at least one injection.

According to another embodiment, a method of generating intervertebral disc-like tissue in a human or vertebrate subject is provided. The method includes administering to a subject a composition comprising an effective amount of a human birth tissue material composition to an intervertebral space. According to one embodiment, the birth tissue material composition includes one or more components of the placental organ. According to one embodiment, the one or more of the components of the placental organ can be the placental globe, the umbilical cord, the umbilical cord blood, the chorionic membrane, the amniotic membrane, the Wharton's jelly, the amniotic fluid, and other placental gelatins, cells, or extracellular material.

According to another aspect, a kit for treating degenerative disc disease is provided that includes the composition as provided herein. The kit may also include at least one delivery device. The kit may further include a set of instructions for use thereof.

BRIEF DESCRIPTION OF THE DRAWINGS

FIG. 2 provides a batch volume and fill calculation sheet according to one embodiment; and FIG. 3 provides a solution calculation sheet according to one embodiment.

DETAILED DESCRIPTION OF THE INVENTION

Figure 1:
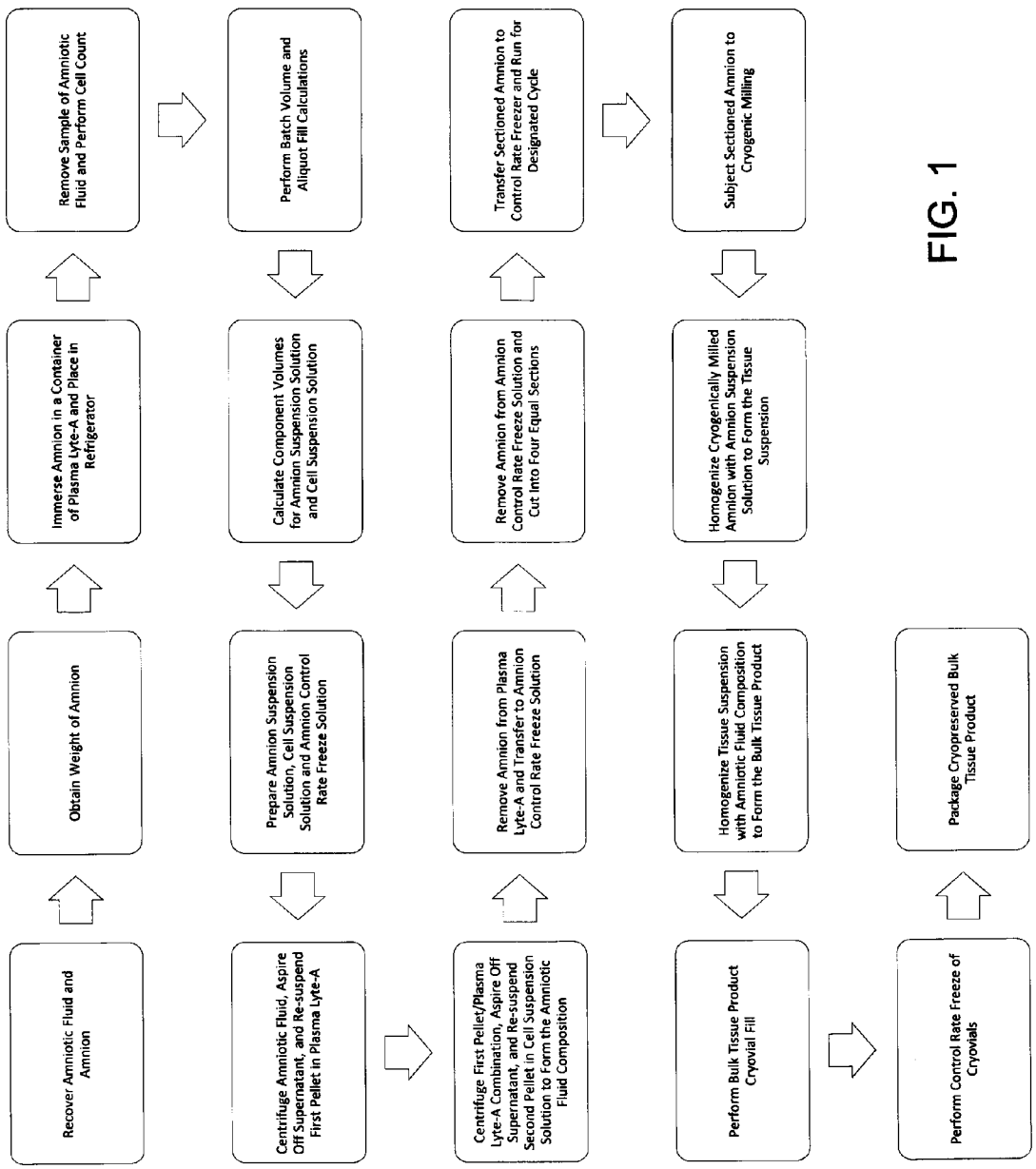
FIG. 1 is a schematic providing an overview of the method of preparing a human birth tissue material composition according to one embodiment.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, "human birth tissue" encompasses one or more of the components of the placental organ including, but not limited to, the placental globe, the umbilical cord, the umbilical cord blood, the chorionic membrane, the amniotic membrane, the Wharton's jelly, the amniotic fluid, and other placental gelatins, cells, and extracellular material.

As used herein, "placental tissue components" encompass one or more of the tissue components of the placental organ including, but not limited to, the placental globe, the umbilical cord, the umbilical cord blood, the chorionic membrane, the amniotic membrane, the Wharton's jelly and other placental gelatins, cells and extracellular material.

As used herein, the term "amnion" and "amniotic membrane" are used interchangeably.

As used herein, the term "intervertebral disc-like tissue" refers to any tissue suitable for the repair or replacement of intervertebral disc tissue or a part thereof.

As used herein, the term "effective amount" refers to an amount of a particular composition sufficient to elicit the desired therapeutic effects.

A method of treating degenerative disc disease in a subject is provided. The method includes the step of administering a human birth tissue material composition onto or into at least one intervertebral disc or one intervertebral space in need of treatment. The birth tissue material composition comprises one or more of the components of the placental organ, including but not limited to, the placental globe, the umbilical cord, the umbilical cord blood, the chorionic membrane, the amniotic membrane, the Wharton's jelly, the amniotic fluid, and other placental gelatins, cells and extracellular material.

A method of generating intervertebral disc-like tissue in a human or vertebrate subject is provided. The method includes administering to a subject a composition comprising an effective amount of a human birth tissue material composition to an intervertebral space for the in situ generation of intervertebral-like tissue. According to one embodiment, the birth tissue material composition includes one or more components of the placental organ. According to one embodiment, the one or more of the components of the placental organ can be the placental globe, the umbilical cord, the umbilical cord blood, the chorionic membrane, the amniotic membrane, the Wharton's jelly, the amniotic fluid, and other placental gelatins, cells, or extracellular material.

The birth tissue material composition administered in the methods of the present invention may be prepared as provided herein. One embodiment of a method for preparing a birth tissue material composition is provided in the schematic of FIG. 1. The method of preparing a human birth tissue material composition includes the step of recovering placental tissue components and amniotic fluid from a seronegative, healthy human. Potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious.disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term Cesarean delivery of a newborn. Alternatively, human birth tissue is recovered from a full-term vaginal delivery of a newborn. The subsequent steps of preparing the human birth tissue material are performed in a controlled environment (i.e., certified biological safety cabinet, hood or clean room). Instruments, solutions, and supplies coming into contact with the human birth tissue material during processing are sterile. All surfaces coming in contact with the human birth tissue material intended for transplant are either sterile or draped using aseptic technique.

Once recovered, one or more of the placental tissue components can be removed via a sterile saline solution rinse, blunt dissection, scalpel, or a combination thereof, if necessary. According to one embodiment, the placental globe, umbilical cord, chorionic membrane, and other gelatins, fluids, cells and extracellular matrix are removed and discarded, leaving the amniotic membrane for further processing. In a preferred embodiment, the human birth tissue material is subject to the method of preparation described herein no more than four hours after recovery to preserve cell viability.

The retained placental tissue components can be placed in a sterile transport solution after aseptic recovery. The sterile transport solution is used to provide an advantageous medium to the natural function of the placental tissue components prior to processing. For example, calcium-rich water can be used as the sterile transport solution to provide a medium to drive undifferentiated cells to become osteogenic when implanted. Throughout the preparation of the human birth tissue material, various methods can be used to drive undifferentiated cells to differentiate into specialized cell types including, but not limited to, transport solutions, soaks, particular temperature ranges, and hyperbaric pressure.

The sterile transport solution preferably includes sodium chloride (NaCl) in a concentration range from typically about 10% to typically about 20% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water.

Amniotic fluid can be placed in a sterile container after aseptic recovery. In a preferred embodiment, a cell count is performed on the amniotic fluid using methods commonly known in the art (e.g., hemocytometer). The amniotic fluid is preferably mixed thoroughly before a sample is taken to ensure that the sample is representative of the number of cells dispersed throughout the amniotic fluid. Additionally, an appropriate dilution of the mixture with regard to the number of cells to be counted can be utilized. The total cell count per milliliter can then be calculated. In another embodiment, a cell counter can be used to determine total cell count per milliliter of fluid. After the cell count is determined, a requisite cell suspension solution volume can be calculated and prepared. The cell suspension volume may be calculated from predetermined requirements for the minimum starting gram weight of tissue per mL of bulk tissue product. In an alternate embodiment, the cell suspension volume may be calculated from predetermined requirements for the minimum number of amniotic fluid cells per 1.0 mL aliquot of bulk tissue product. In one embodiment, the cell suspension solution includes typically about 91% volume of Plasma Lyte-A and typically about 9% volume of human albumin 25% solution.

In a preferred embodiment, after the cell count is completed, an amniotic fluid composition is prepared according to the following steps. Particles in the amniotic fluid are separated from the liquid component of the amniotic fluid using centrifugation. The resulting, separated particles are referred to as "pellets." The separation of particles from the liquid component of the amniotic fluid may occur by any art-recognized method including sedimentation or microfiltration. In a preferred embodiment, the amniotic fluid is evenly aliquoted into sterile conical centrifuge tubes. The amniotic fluid can be distributed in equal amounts in as many tubes as necessary for the volume recovered. The amniotic fluid can be centrifuged at 200 rpm to 15,000 rpm for a period of up to 30 minutes at ambient temperature. In one embodiment, the amniotic fluid is centrifuged at approximately 1410 rpm (400×gravity [RCF]) for a period of 10 minutes at ambient temperature. Using a sterile pipette, the supernatant can be aspired from each tube and discarded. An isotonic solution can be used to re-suspend each pellet and bring the volume of each tube up to a predetermined amount. In one embodiment, the isotonic solution is Plasma Lyte-A. The pellet/isotonic solution combination can be centrifuged at 200 rpm to 15,000 rpm for a period of up to 30 minutes at ambient temperature. In one embodiment, the pellet/isotonic solution combination is centrifuged at approximately 1410 rpm (400×g [RCF]) for a period of 10 minutes at ambient temperature. Using a sterile pipette, the second supernatant can be aspired from each tube and discarded. Each second pellet can be re-suspended in a cell suspension solution of a predetermined amount to form the amniotic fluid composition. In one embodiment, the cell suspension solution includes Plasma Lyte-A and human albumin 25% solution. In a preferred embodiment, the cell suspension solution includes typically about 91% volume of Plasma Lyte-A and typically about 9% volume of human albumin 25% solution. The cells in each tube can be thoroughly suspended by using a vortex mixer for a minimum of three seconds. Immediately thereafter, the contents of each tube are homogenized with a cell suspension solution to form the amniotic fluid composition. In a preferred embodiment, the cell suspension solution includes typically about 91% volume of Plasma Lyte-A and typically about 9% volume of human albumin 25% solution.

In one embodiment, the discarded first and second supernatant from the aforementioned amniotic fluid composition preparation steps are further precipitated using dialysis equipment or micropore/nucleopore filters. Alternately, the first and second supernatant can be further precipitated by pipetting the supernatants onto sterile wax paper, heating the contents to quickly evaporate the liquid, and then adding the remaining material back into the final amniotic fluid composition. This method allows for the removal of the extraneous liquid, while maximizing the cells, proteins and other particles otherwise discarded in the first and second supernatants. The remaining material precipitated from the first and second supernatants can be homogenized with the amniotic fluid composition.

After the amniotic fluid composition is generated, a second cell count can be performed on a representative sample using a hemocytometer, a cell counter, or any other method commonly known in the art. The amniotic fluid preparation can be stored at typically about 1-10° C. for a period of up to 24 hours pending further processing.

A predetermined percentage of the amniotic fluid composition (representative sample) can be retained for testing and not included in the final bulk product. This representative sample can be retained for analysis and comparison to the cells in the final bulk product to discern any deleterious effects on the amniotic fluid cells, particularly the effects of the cryoprotectant(s) on the amniotic fluid cells in the final bulk product and/or the effects of cleaning, processing, freezing and thawing on the amniotic fluid cells.

Simultaneous with the initial cell count of the amniotic fluid, the weight of the placental tissue components can be determined. Thereafter, the placental tissue components can be transferred aseptically to a sterile dish containing Plasma Lyte-A and stored in a quarantine refrigerator pending further processing.

After the weight of the placental tissue components is determined, a requisite tissue suspension solution volume can be calculated and prepared based on predetermined requirements for the minimum starting gram weight of tissue per mL of bulk tissue product. In one embodiment, the tissue suspension solution comprises Plasma Lyte-A, human albumin 25% solution, and dimethyl sulfoxide. In a preferred embodiment, the tissue suspension solution comprises: typically about 44% volume of Plasma Lyte-A, typically about 36% volume of human albumin 25% solution, and typically about 20% volume of dimethyl sulfoxide.

In one embodiment, the total number of final product units can be calculated based on predetermined requirements for: (1) the minimum starting tissue gram weight per mL of bulk tissue product; and (2) the minimum number of amniotic fluid cells per 1.0 mL aliquot of bulk tissue product. In a preferred embodiment, the total number of final product units can be calculated based on predetermined requirements for the minimum starting tissue gram weight per mL of bulk tissue product. In one embodiment, the final product vials can be of various volumes such as, for example, 0.25 mL, 0.50 mL, 1.0 mL, 1.25 mL, 2.0 mL, 3.0 mL or any other volume as contemplated by one of ordinary skill in the art.

In one embodiment, the placental tissue components include amniotic membrane. In another embodiment, the placental tissue components include one or more components selected from the group consisting of amniotic membrane, chorionic membrane, Wharton's jelly, umbilical cord tissue, umbilical cord blood, placental globe, and other gelatins, other cells and extracellular matrix from placental tissue components. The placental tissue components can them be placed in a sterile dish containing Plasma Lyte-A until further processing.

The placental tissue components can be removed from the Plasma Lyte-A and cryopreserved according to methods commonly used in the art. The placental tissue components can be soaked in cryoprotectant prior to cryopreservation. In one embodiment, the cryoprotectant is one commonly used in the industry, such as, for example, dimethyl sulfoxide (DMSO). In a preferred embodiment, the cryoprotectant is an amnion control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. Any cryoprotectant specific to the birth tissue material described herein may be used. In one embodiment, cryopreservation is achieved using a controlled rate freezer, resulting in a 1° C. rate from nucleation to −35° C. and a 10°

C. per minute cooling rate to a −90° C. end temperature. However, any cryopreservation method commonly known in the art may be used.

After cryopreservation, the placental tissue components are subjected to morselization. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used. In one embodiment, the total number of final product units can be calculated based on predetermined requirements for: (1) the minimum tissue gram weight after morselization per mL of bulk tissue product; and (2) the minimum number of amniotic fluid cells per 1.0 mL aliquot of bulk tissue product. In an alternate embodiment, the total number of final product units can be calculated based on predetermined requirements for the minimum tissue gram weight after morselization per mL of bulk tissue product.

After morselization, the milled placental tissue components can be combined with the tissue suspension solution to form a tissue suspension. In one embodiment, the tissue suspension solution includes Plasma Lyte-A, human albumin 25% solution, and dimethyl sulfoxide, which is used immediately to prepare the final bulk tissue product. In a preferred embodiment, the tissue suspension solution comprises typically about 44% volume of Plasma Lyte-A, typically about 36% volume of human albumin 25% solution, and typically about 20% volume of dimethyl sulfoxide, which is used immediately to prepare the final bulk tissue product. In an alternate embodiment, the tissue suspension solution includes typically about 44% volume of Plasma Lyte-A and typically about 36% volume of human albumin 25% solution. The 20% volume of dimethyl sulfoxide is purposefully withheld pending final combination of the bulk tissue product. In this alternate embodiment, the milled tissue suspension (without dimethyl sulfoxide) can be stored at about 1-10° C. for a period of up to about 24 hours, pending further processing. In the alternate embodiment, the 20% volume of dimethyl sulfoxide can be added to the tissue suspension immediately prior to final bulk tissue product manufacture.

Bulk tissue product can be manufactured by homogenizing the amniotic fluid composition and the tissue suspension. Both the amniotic fluid composition and the tissue suspension can be vortexed for no less than about three seconds prior to combination. In a preferred embodiment, the bulk tissue product can be homogenized using a laboratory homogenizer mixer, followed by continuous mixing with magnetic stirrers. Immediately thereafter, the bulk tissue product can be placed on cold packs and individual, empty cryovials can be filled with the bulk tissue product. In one embodiment, the final product vials can be of various volumes such as, for example, 0.25 mL, 0.50 mL, 1.0 mL, 1.25 mL, 2.0 mL, 3.0 mL or any other volume as contemplated by one of ordinary skill in the art. Cryopreservation of the final bulk tissue product vials can be achieved through control-rate freezing by methods commonly known in the art.

Representative samples from the beginning, middle, and end of the cryovial fill cycle can be removed from the final product count for quality control testing, including, but not limited to, bioburden testing, *mycoplasma* DNA by polymerase chain reaction, and bacterial endotoxin test (Limulus Ameboycte Lysate). Representative samples from the beginning, middle, and end of the cryovial fill cycle can be removed from the final product count to store for future testing should the need arise.

Another embodiment of a method for preparing a birth tissue material composition is provided herein. According to one embodiment, the composition includes human placental tissue components. The composition can optionally include an acceptable carrier composition. The human placental tissue components can be prepared according to the steps provided herein. In certain embodiments, the human placental tissue components can be combined with the carrier composition to formulate a composition suitable for application onto or into an intervertebral disc or an intervertebral space affected with degenerative disc disease.

To prepare the human placental tissue components for inclusion in a composition, placental tissue components are initially recovered from a seronegative, healthy woman per the aforementioned donor screening procedures, including a comprehensive medical history and behavior risk assessment, physical exam and infectious disease testing.

Placental tissue is preferably recovered from a full-term Cesarean delivery of a newborn. Alternatively, placental tissue is recovered from a full-term vaginal delivery of a newborn. The subsequent steps of preparing the placental tissue components are performed in a controlled environment (i.e., certified biological safety cabinet, hood or clean room). Instruments, solutions, and supplies coming into contact with the human placental tissue material during processing are sterile. All surfaces coming in contact with the human placental tissue material intended for transplant are either sterile or draped using aseptic technique.

According to one embodiment, the human placental tissue components can include one or more components selected from the group consisting of amniotic membrane, chorionic membrane, Wharton's jelly, umbilical cord tissue, umbilical cord blood, placental globe, and other gelatins, other cells and extracellular matrix from placental tissue. Other variations of the invention include, however, removing one or more of the amniotic membrane, chorionic membrane, Wharton's jelly, umbilical cord tissue, umbilical cord blood, placental globe, and other gelatins, other cells and extracellular matrix from placental tissue before further processing. In a preferred embodiment, the placental tissue components include amniotic membrane only. Removal of one or more of the placental tissue components can be achieved via a sterile saline solution rinse, blunt dissection, scalpel, or a combination thereof, if necessary.

The retained placental tissue components can be placed in a sterile transport solution after aseptic recovery. The sterile transport solution is used to provide an advantageous medium to the natural function of the placental tissue components prior to processing. Throughout the preparation of the human placental tissue composition, various methods can be used to drive undifferentiated cells to differentiate into specialized cell types including, but not limited to, transport solutions, soaks, particular temperature ranges, and hyperbaric pressure.

The sterile transport solution preferably includes sodium chloride (NaCl) in a concentration range from typically about 0.9% to typically about 20% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water.

After delivery to the processing facility, the weight of the placental tissue components can be determined. Thereafter, the placental tissue components can be transferred aseptically to a sterile dish containing Plasma Lyte-A and stored in a quarantine refrigerator pending further processing.

The placental tissue components can be removed from the Plasma Lyte-A and cryopreserved according to methods commonly used in the art. The placental tissue components can be soaked in cryoprotectant prior to cryopreservation. Various cyroprotectants are often used to avoid the formation of ice crystals and/or delay the onset of ice formation to the lowest temperature possible. Such cryoprotectants known in the art are typically glycerol, dimethyl sulfoxide (DMSO), dimethyl acetamide, methanol, ethylene glycol, propylene glycol, trimethylamine acetate, and other high molecular weight solutes capable of forming strong hydrogen bonds to water, which may be used singularly or in combination thereof. In one embodiment, the cryoprotectant is dimethyl sulfoxide (DMSO) at a concentration of about 10% (v/v). In a preferred embodiment, the cryoprotectant is an amnion control rate freeze solution comprising Plasma Lyte-A, human albumin 25% solution, and dimethyl sulfoxide. In another embodiment, the cryoprotectant is a commercially available cryoprotectant such as Synth-a-Freeze® available from Invitrogen. However, any cryoprotectant specific to the placental tissue components described herein may be used. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

According to one embodiment, after cryopreservation, the placental tissue components are subjected to morselization. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used.

After morselization, the milled placental tissue components can be homogenized with a tissue suspension solution to form the final product. In one embodiment, the tissue suspension solution includes Plasma Lyte-A, human albumin 25% solution, and dimethyl sulfoxide. In a preferred embodiment, the tissue suspension solution comprises typically about 67.5% volume of Plasma Lyte-A, typically about 22.5% volume of human albumin 25% solution, and typically about 10% volume of dimethyl sulfoxide. In another embodiment, the tissue suspension solution comprises typically about 0.01%-10% volume of dimethyl sulfoxide combined with a medium or buffer, including, but not limited to, sodium chloride, glycerol, methylcellulose or appropriate buffer solutions, e.g., phosphate buffered saline.

Final product can be manufactured by homogenizing the placental tissue components and the tissue suspension solution. In a preferred embodiment, the final product can be homogenized using a laboratory homogenizer mixer, followed by continuous mixing with magnetic stirrers. Immediately thereafter, the final product can be placed on cold packs and aliquoted into individual, empty cryovials. In one embodiment, the final product can be of various volumes such as, for example, 0.25 mL, 0.50 mL, 1.0 mL, 1.25 mL, 2.0 mL, 3.0 mL or any other volume as contemplated by one of ordinary skill in the art. Cryopreservation of the final bulk tissue product vials can be achieved through control-rate freezing by methods commonly known in the art.

Representative samples from the beginning, middle, and end of the cryovial fill cycle can be removed from the final product count for quality control testing, including, but not limited to, bioburden testing, *mycoplasma* DNA by polymerase chain reaction, and bacterial endotoxin test (Limulus Ameboycte Lysate). Representative samples from the beginning, middle, and end of the cryovial fill cycle can be removed from the final product count to store for future testing should the need arise.

In one embodiment, the total number of final product units can be calculated based on predetermined requirements for the minimum starting tissue gram weight per mL of final product. In an alternate embodiment, the total number of final product units can be calculated based on predetermined requirements for the minimum tissue gram weight after morselization per mL of final product.

Another embodiment of a method for preparing a birth tissue material composition is provided herein. According to one embodiment, the composition includes human placental tissue components. In some aspects, the placental tissue components may be subjected to morselization following recovery. As used herein, "morselization" means to grind up to particle form. Tissue morselization may occur by any art-recognized method of tissue disruption, including, but not limited to, milling, blending, sonicating, homogenizing, micronizing, pressing, pulverizing, triturating, macerating, or a combination thereof. Particles may be micron or submicron size. The resulting product may be a dry powder. In some embodiments, the morselized placental tissue components are dissolved in one or more biocompatible solvents to create a paste, emulsion, suspension or solution. This dissolution may occur during the manufacturing process or immediately prior to application. Examples of biocompatible solvents include, but are not limited to, physiological saline; BSS™, a balanced salt solution containing per ml 0.64% sodium chloride, 0.075% potassium chloride, 0.048% calcium chloride, 0.03% magnesium chloride, 0.39% sodium acetate, and 0.17% sodium citrate dihydrate, as well as sodium hydroxide and/or hydrochloric acid to adjust pH, and water; Ocular Irrigation Solution™, Lactated Ringer's solution; normal saline solution; or normal saline adjusted to pH 7.4 with sodium bicarbonate.

In some embodiments, the placental tissue components are morselized by use of a tissue grinder (e.g., a Potter-Elvehjem grinder or a Wheaton Overhead Stirrer). In some embodiments, the placental tissue components are micronized by use of a sonicator. In some embodiments, the placental tissue components are micronized by use of a bead beater. In some embodiments, the placental tissue components are micronized by use of a freezer/mill (e.g., a SPEX SamplePrep Freezer/Mill). In some embodiments, the placental tissue components are micronized by manual use of a pestle and mortar. The placental tissue components may be optionally lyophilized before or after being subjected to micronization.

According to one embodiment, the birth tissue material composition can be formulated into an injectable form. An injectable formulation can include the compositions as described herein either alone or in combination with a suitable carrier. The carrier can include any variety of components suitable for application onto or into an affected intervertebral disc or intervertebral space. According to one embodiment, the carrier composition includes one or more vitamins, minerals, proteins, fats, collagens (including collagen extracted from the placental globe), hyaluronic acid, waxes, glycols and derivatives thereof, glycerols and derivatives thereof, oils (including essential oils), fatty acids, cholesterols, alcohols, emollients, adsorbents, lubricants, emulsifying agents, thickening agents, humectants, surfactants, pharmaceutical ingredients, preservatives, antifungal agents, antioxidants, antimicrobial agents, structuring agents, dispersing agents, pH-adjusting components, sequestering or chelating agents, wetting agents, coloring agents, and other components known in the art to be suitable for use in a composition that can be applied onto or within the human body. The optional carrier composition can be formulated in such a way that the combination of the human birth tissue material composition and the carrier composition are chemically compatible and do not form complexes which precipitate from the final composition.

According to one embodiment, the human birth tissue material composition and the carrier composition as provided herein can be mixed or blended according to a variety of conventional techniques. According to one embodiment, the human birth tissue material composition and the carrier composition can be mixed in a manner to produce a smooth and homogenous composition. According to one embodiment, the human birth tissue material composition as provided herein is introduced to the carrier composition after the carrier composition is formed (i.e., post-added). In an alternative embodiment, the human birth tissue material composition is introduced during carrier composition preparation. The amount of placental tissue present in the composition can vary depending upon whether a carrier composition is utilized, the frequency of use, and the treatment desired. The amount of carrier composition present in the final composition can vary according to the final formulation of the composition. According to one embodiment, the carrier composition components can be present in an amount from typically about 0.1% to about 99.0% based on total composition weight.

The human birth tissue material compositions as described herein may be administered by any routes of administration commonly known in the art. Particularly preferred routes of administration include direct injection of the composition onto or into an intervertebral disc and/or intervertebral space or direct application of the composition onto or into an intervertebral disc and/or intervertebral space during surgery. In some embodiments, the composition is administered by direct injection following discectomy and placement of a vertebral body spacer, particularly following discectomy and fusion surgery where the grafted material has not been well-tolerated by the subject or the vertebral fusion has not been successful. In such embodiments, the composition may be directly injected into an intervertebral space formed by an existing vertebral body spacer. In another embodiment, the human birth tissue material composition may be used as a coating for the vertebral body spacer.

According to one embodiment, the injectable formulation may be delivered via a single injection or multiple injections may be administered either to a single site or to more than one site on or around the one or more diseased intervertebral discs. Multiple administrations may occur essentially at the same time or separated in time.

According to one embodiment, the human birth tissue material compositions as described herein can be optionally introduced to a diseased vertebral space via a delivery device (e.g., vertebral body spacer, balloon). The delivery device is capable of retaining and delivering a therapeutically effective amount of the human birth tissue material composition as described herein, optionally in combination with an acceptable carrier. The delivery device may be further capable of retaining and delivering autograft or allograft bone, bone fragments or bone substitute material to prevent the vertebrae from collapsing and to increase stability. The geometry of the delivery device corresponds to the geometry of the required intervertebral space between the vertebral bodies. The size and shape of the delivery device may vary according to the location of the diseased areas within the vertebral column. Modification of the delivery device may be made to adjust the size and shape of the spacer to the gender, size and age of the subject or the requirements to relieve a particular type of degenerative disc disease. The delivery may, optionally, include a fixing means attached thereto (e.g., a pin, screw, wire, brace or plate) to aid in maintaining the delivery device in a fixed position on the vertebral column.

According to one embodiment, the delivery device is formed from a bioresorbable material such that the need for a second surgery to remove the delivery device is eliminated. According to one embodiment, the delivery device is formed from polylactide or polyglycolic acid. According to a preferred embodiment, the delivery device is formed from an umbilical cord, an umbilical cord vein, or an umbilical cord artery.

In an alternative embodiment, the delivery device may be formed from a combination of a non-resorbable material and bioresorbable material (e.g., a body or support of a non-bioresorbable material coated with a bioresorbable material) which, together, may provide adequate structural support to substantially maintain the intervertebral space between the vertebral bodies subject to treatment (i.e., prevent collapse). According to either delivery device embodiment, the delivery device itself may be coated with a composition comprising one or more biologically active agents as provided herein.

A person skilled in the art in the field of orthopedic surgery, particularly one specializing in the spine, will appreciate that many variations may be made in the procedure to implant the delivery device. According to one embodiment, the delivery device is capable of insertion through a posterior or postero-lateral surgical approach to the spine via a unilateral trans-facetal approach to the disc. Alternatively, the delivery device may be inserted through the anterior, antero-lateral, or lateral approach to the spine and the intervertebral disc.

According to one embodiment, any existing intervertebral disc tissue is initially removed from between a first vertebral body and second vertebral body in need of treatment. Next, the delivery device is placed between the first vertebral body and the second vertebral body thereby forming an intervertebral space between the first and second vertebral bodies.

According to one embodiment, the delivery device is preloaded with a therapeutically effective amount of the human birth tissue material composition as described herein. According to an alternative embodiment, a human birth tissue material composition may be administered (e.g., injected) to the delivery device once the device has been placed into the desired position.

The human birth tissue material compositions as described herein can be utilized in the treatment of degenerative disc diseases including, but not limited to, degenerated discs, bulging discs, herniated discs, thinning discs, collapsed discs, osteophytes (e.g., bone spurs), spontaneous or post-traumatic tears of the disc tissue and other observable disc irregularities. Specific examples include, but are not limited to, lumbar and cervical spinal stenosis and spondylosis, fibrosis, arthritis or osteoporosis.

The human birth tissue material compositions as described herein can be optionally mixed with or administered in combination with bioactive agents such as inflammatory inhibitors, antibiotics, cytokines, minerals, growth factors (e.g., fibrin and/or thrombin), wound healing agents, hyaluronic acid, cellular attractant and scaffolding reagents (e.g., fibronectin) antibiotics, chemotherapeutic agents, antigens, antibodies, enzymes, NSAIDs, muscle relaxants, vectors for gene delivery and hormones.

As described herein, the human birth tissue material compositions can be formulated as a solid, semi-solid or liquid. Suitable formulations may include, but are not limited to, a cream, emulsion, spray, gel, ointment, salve, butter, gel, putty, balm, or pliable stick. In one embodiment, the gel or putty carrier could be achieved through collagen extracted from the placental globe.

Also provided is a kit for treating degenerative disc disease that includes an effective amount of a composition as described herein. Such kits can include a package that is adapted to receive one or more containers, at least one of the container(s) including a composition as described herein. Containers can include a vial or other types of containers such as glass or injection or blow-molded plastic containers. In certain embodiments, the container can be a vial that contains sufficient volume of composition for one (i.e., single use) or more injections. The kit is appropriately preserved up until and during shipment to a distributor, medical facility, or other end user. According to a preferred embodiment, the kit may include at least one delivery device as described herein. The kit can additionally include at least one set of instructions for the end user, including an explanation of how to inject or otherwise deliver and maintain the composition.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

Example 1

The placental construct may be prepared according to the method of FIG. 1, the details of which are herein provided.

Human birth tissue was obtained from a seronegative, healthy mother via Cesarean section. To maximize the overall quality of the donated tissue, a recovery technician was present in the operating room during the donor's Cesarean section to assist the surgical team with recovery, treatment and handling of the birth tissue. The donor was surgically prepped and draped per AORN standards prior to the Cesarean section procedure. The recovery technician prepared the recovery site by establishing a sterile field on a back table in the operating room.

Amniotic fluid was recovered according to the following procedures provided herein. The physician's assistant cleared all maternal blood from the surgical site. A suction cannula was positioned directly above the intended amnion/chorion membrane incision site. Using the smallest appropriate incision, the amniotic and chorionic membranes were breached, releasing the amniotic fluid into the suction cannula. Avoiding maternal blood, the physician's assistant suctioned as much amniotic fluid volume as possible into a sterile suction canister. Immediately following recovery, the sterile suction canister was transferred to the sterile back table. The recovery technician examined the amniotic fluid for the presence of visible blood. After noting that no visible blood was present, the recovery technician aseptically transferred the amniotic fluid to a sterile Nalgene jar and performed swab cultures. The recovery technician secured the lid on the Nalgene jar to which the appropriate identification was affixed.

Following delivery of the baby, the physician's assistant placed the human birth tissue en-bloc into a sterile basin. Maintaining sterility, the basin was transferred to the recovery technician onto the sterile field on the back table. Beginning at the amnion/chorion membrane surgical incision site, the recovery technician used blunt dissection to separate the chorionic membrane from the amniotic membrane, using care not to tear the amniotic membrane. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 mL of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed.

The Nalgene jar containing the amniotic fluid and the plastic transport container containing the amniotic membrane were placed in a qualified shipping container with an appropriate amount of wet ice to maintain refrigerated temperatures. The validated box arrived at the processing facility approximately one hour following recovery and was immediately inspected per standard operating procedures and placed in refrigerated temperatures (1-10° C.).

Processing was performed on a sterile field using aseptic technique in a validated cleanroom at the processing facility less than four hours after the recovery was completed. All manufacturing steps were recorded concurrently by a circulating technician on a designated processing record.

Amniotic Membrane Preparation

The amniotic membrane was removed from the plastic transport container and outer bag. The inner bag containing the amniotic membrane was aseptically passed onto a sterile field. Approximately 35 mL of the sterile transport solution was aspirated out of the bag utilizing a sterile pipette. Subsequently, the sample was transferred to a sterile conical tube for pre-processing bioburden testing. Using sterile forceps, the amniotic membrane was removed from the inner bag and placed in a sterile basin on a sterilely draped pre-set balance. The weight of the amniotic membrane was recorded. The sterile basin containing the amniotic membrane was transferred to a back table. Approximately 250 mL of Plasma Lyte-A was added to a second sterile basin and covered with the corresponding sterile lid. Using sterile forceps, the amniotic membrane was removed from the first sterile basin and transferred to a sterile prep board where the membrane was spread flat. Using a sterile lap sponge, any remaining debris/blood was removed from the surface of both sides of the amniotic membrane. The amniotic membrane was subsequently transferred to a second sterile basin containing Plasma Lyte-A where the membrane was covered, labeled and transferred to a quarantine refrigerator.

Amniotic Fluid Preparation

Sterile pipettes and 50 mL sterile conical centrifuge tubes were transferred to a sterile field. The Nalgene jar was moved in a gentle swirling motion to ensure cells were equally dispersed throughout amniotic fluid prior to removal of samples. The Nalgene jar containing the amniotic fluid was opened, and 10 mL of amniotic fluid was aspirated out utilizing a sterile pipette and transferred to a sterile conical tube for pre-processing bioburden testing. Approximately one mL of amniotic fluid was aspirated out utilizing a sterile pipette in order to complete the cell count. Utilizing a sterile 50 mL pipette, the remaining amniotic fluid was aseptically aspirated out of the Nalgene jar and transferred into 50 mL conical centrifuge tubes. Aliquots of the amniotic fluid were aseptically distributed in equal amounts in an even number of 50 mL sterile conical centrifuge tubes.

Batch Volume and Aliquot Fill Calculation

The batch volume and aliquot fill calculations (See FIG. 2) were determined based on the following calculations.
1. Record Amnion Weight (AW) in grams.
2. Calculate Amnion Allowable Aliquots (AA).
    2.1 Divide Amnion Weight (AW) by minimum starting amnion gram weight per 1 mL aliquot (0.03 grams) to calculate total Amnion Allowable Aliquots (AA).
3. Calculate Cell Count
    3.1 Record the total Amniotic Fluid Volume (A) in mL.
    3.2 Record the Total Cells Counted (B) for the four large corner squares and the middle square of the hemocytometer counting grid using the hemocytometer and an inversion microscope per standard operating procedures.
    3.3 Calculate Average Cells/Square (C).
        3.3.1 (C)=Total Cells Counted (B)/5 Squares Counted
    3.4 Record Dilution Factor used in preparation of cell count (D).
    3.5 Calculate the Total Cell Density (cells/mL) (E).
        3.5.1 $(E)=(C)\times(D)\times10^4$
    3.6 Calculate Total Cells (TC).
        3.6.1 Total Cells (TC)=Total Cell Density (E)×Total Volume of Amniotic Fluid (A)
4. Calculate Aliquot Cell Density (CD) (Aliquot=1 mL).
    4.1 (CD)_mL=Total Cell (TC)/Amnion Allowable Aliquot (AA)
5. Determine Bulk Product Volume (BV).
    5.1 (AA) Amnion Allowable Aliquots=Bulk Product Volume (BV)
6. Determine Lot Vial Fill Calculations.
    6.1 Record Bulk Product Volume (BV)
    6.2 Record the target vial production per size provided by management.
    6.3 Calculate Total Vial Target
    6.4 Calculate Total Volume Requirement for Vial Target.
        6.4.1 [Vial Target for 0.25 mL vials]×0.25=Volume Requirement (mL) for 0.25 mL Vials
        6.4.2 [Vial Target for 0.50 mL vials]×0.50=Volume Requirement (mL) for 0.5 mL Vials
        6.4.3 [Vial Target for 1.25 mL vials]×1.25=Volume Requirement (mL) for 1.25 mL Vials
    6.5 Calculate Total Vial Fill Volume.
    6.6 Compare Bulk Product Volume to Total Vial Fill Volume requirement based on the production plan.
        6.6.1 Total Vial Fill Volume must be ≤ Bulk Product Volume (BV).
        6.6.2 Adjust vial targets accordingly.

Solutions Calculations

After obtaining the Bulk Product Volume (BV), the component volumes for the tissue suspension solution (i.e., amnion suspension solution) and the cell suspension solution were determined based on the following calculations (See FIG. 3).
1.0 Bulk Product Volume (mL) (BV)=Total Suspension Solution Volume (mL) (SS)
2.0 Calculate Cell Suspension Solution Volume (CS)
    2.1 (CS)=Total Suspension Solution Volume (SS)/2
    2.2 Calculate (CS) Component Volume(s) Required:
        2.2.1 Plasma Lyte-A Volume (mL)=(CS)×0.91
        2.2.2 Human Albumin 25% Solution Volume (mL)=(CS)×0.09
    2.3 Calculate Amnion Suspension Solution (AS)
        2.3.1 (AS)=Total Suspension Solution Volume (SS)/2
        2.3.2 Calculate (AS) Component Volume(s) Required:
            2.3.2.1 Plasma Lyte-A Volume (mL)=(AS)×0.44
            2.3.2.2 Human Albumin 25% Sol. Volume (mL)=(AS)×0.36
            2.3.2.3 Dimethyl Sulfoxide, USP Volume (mL)=(AS)×0.20

Solution Preparations

The following materials were transferred to the sterile field: (i) Human Albumin 25% Solution, Excipient, EU Grade; (ii) Plasma Lyte-A Injection (pH 7.4); and (iii) DMSO (dimethyl sulfoxide), USP. In separate 1 L sterile containers, the cell suspension solution and the amnion suspension solution were prepared based on the calculations obtained utilizing the solution calculations sheet set forth in FIG. 3. The amnion control rate freeze solution was prepared according to the directions as set forth in FIG. 3. The containers were labeled with respective solution names, lot numbers, and expiration dates and stored at 1-10° C. pending further use.

Aseptic Processing of Amniotic Fluid Composition

Amniotic fluid-filled conical tubes were aseptically transferred to an Eppendorf centrifuge and centrifuged at 400×g for 10 minutes at ambient temperature. At the completion of each cycle, the conical tubes were aseptically transferred back to the sterile field. Each conical centrifuge tube was checked by a processing technician to ensure a pellet had formed. The results were recorded in the batch record. The supernatant was removed and discarded using a sterile pipette, and a sufficient volume of Plasma Lyte-A was added to each conical tube to re-suspend the pellet and increase the volume in each tube to approximately 20 mL. Each tube was placed on a vortex mixer for 3-5 seconds to fully re-suspend the pellets. The contents of the conical centrifuge tubes were subsequently combined, reducing the overall conical centrifuge tube number by half by quickly pouring the suspension from a first tube to a second tube, ensuring maximum transfer of cells during combination. The process was repeated until all remaining conical centrifuge tubes were combined, reducing the number of tubes by half. The remaining conical centrifuge tubes were aseptically transferred to an Eppendorf centrifuge and centrifuged at 400×g for 10 minutes at ambient temperature. At the completion of each cycle, the conical tubes were aseptically transferred back to the sterile field. Each conical centrifuge tube was checked by a processing technician to ensure a pellet had formed. The results were recorded in the batch record. The supernatant was removed and discarded using a sterile pipette, and a sufficient volume of cell suspension solution was added to each conical tube to re-suspend the pellet and increase the volume in each tube to approximately 20 mL. Each tube was placed on a vortex mixer for 3-5 seconds to fully re-suspend the pellets. Next, each suspension was quickly poured into the container of cell suspension solution to form the amniotic fluid composition. The amniotic fluid composition was stored in refrigerated temperatures at 1-10° C. until further processing.

Amnion Control Rate Freezing

The following materials were transferred to the sterile field: amnion (in Plasma Lyte-A solution); amnion control rate freeze solution; appropriately sized pipettes; sterile bowl; sterile forceps, sterile tray; and sterile spatula. The amnion was removed from Plasma Lyte-A solution and transferred to the amnion control rate freeze solution. After 30 minutes, the amnion was removed from the amnion control rate freeze solution and transferred to the sterile tray where it was cut into four equal sections. The tray with the sectioned amnion was aseptically transferred to a control rate freezer. A control rate freezer probe was placed near the center of the chamber, taking care not to contact any metal in the chamber. The control rate freezer was activated by selecting a pre-programmed cycle.

Amnion Morselization

The amnion was subjected to morselization by cryogenic milling by the procedures described herein. A Spex Freezer/Mill® was programmed to the following settings: grinding rate=12; cycles=3; pre-cooling time=5 minutes; grinding time=2 minutes; and intermediate cooling=2 minutes. Sterile, autoclaved milling cylinders, impactors and end-caps were placed in an ultra-low freezer for a minimum of 15 minutes in order to pre-cool the materials prior to use. The milling cylinders, impactor and end-caps were removed from ultra-low freezer and aseptically transferred to the sterile field. One end cap was inserted onto each cylinder. The amnion was subsequently removed from the control rate freezer. One amnion section was placed into each of the four cylinders. An impactor bar was placed inside each of the four cylinders. The second end-cap was secured onto each cylinder, sealing the four milling chambers. The milling chambers were placed into the Spex Freezer/Mill® one at a time and allowed to run for the aforementioned program settings. At the conclusion of each milling event, the chamber was removed and immediately aseptically transferred to a sterile field. Using a sterile extractor tool, an end cap was removed from each chamber. The impactor bar and milled amnion were quickly dispensed into a sterile bowl. A sterile spatula was used to remove any remaining milled amnion from the milling cylinder or end-caps. Approximately 100 mL of amnion suspension solution was added to the milled amnion in a sterile bowl. Once thawed, any remaining amnion was removed from the impactor using a sterile spatula. This milling procedure was repeated for each of the four milling chambers until all milled amnion was added to the amnion suspension solution, thereby forming the tissue suspension.

Bulk Tissue Product

A sterile 2 L Erlenmeyer flask was aseptically transferred to a back table. The tissue suspension (amnion suspended in the amnion suspension solution) and the amniotic fluid composition were aseptically poured into the 2 L Erlenmeyer flask. The flask was appropriately covered and labeled. Immediately thereafter, the flask was placed in a quarantine refrigerator at 1-10° C.

Vial Fill

The following materials were transferred to the sterile field: sterile pipettes; sterile cryovial racks; sterile cryovials; and bulk tissue product. The bulk tissue product was removed from the quarantine refrigerator and placed on cold packs on a sterilely draped mixer. A stir bar was aseptically added to the bulk tissue product. The cryovials were filled using a repeater pipette pre-set to target fill volume as indicated in the production plan. Immediately following fill and capping, each cryovial was inspected per quality control (QC) standard operating procedures. Any vials failing QC inspection were discarded per biohazard waste disposal standard operating procedures. The cryovials that passed QC inspection were placed in cryovial racks.

Bulk Tissue Product Cryopreservation

The cryovial racks were transferred to sterile racks and placed in a control rate freezer. A control rate freezer probe was placed near the center of the chamber, taking care not to contact any metal in the chamber. The control rate freezer was activated by selecting a pre-programmed cycle. Upon completion of each control rate freeze, each cryovial was inspected per QC standard operating procedures. Any vials failing QC inspection were discarded per biohazard waste disposal standard operating procedures. The cryovial racks were placed in sterile containers and transferred to a quarantine ultra-low freezer to await results of all lot release testing before final packaging. Representative samples from the beginning, middle, and end of the cryovial fill cycle were removed from the final product count for lot release testing, which included: bioburden testing, *mycoplasma* DNA by polymerase chain reaction, and bacterial endotoxin test (Limulus Ameboycte Lysate).

Packaging of Cryopreserved Bulk Tissue Product

Throughout packaging procedures, the cryovials containing bulk tissue product were exposed to ambient temperature for a time period of one minute or less. After lot release testing clearance, each cryovial was packaged into a sterile foil pouch using aseptic technique. Using an AccuSeal 540Plus sealer, each foil pouch was sealed following standard operating procedures. Following QC inspection, each pouch was packaged in an outer box and labeled with the unique tissue identification number assigned to the cryovial, which was designed to ensure the traceability of the tissue from receipt through clinical use, transfer or destruction. Each cryovial was stored at ultra-low temperatures (≥65° C.) prior to transplantation. Final product vial sizes were 0.25 mL, 0.50 mL, and 1.25 mL.

I claim:

1. A method of treating degenerative disc disease comprising
   administering an effective amount of a human birth tissue material composition onto or into at least one intervertebral disc or at least one intervertebral space in need of treatment,
   wherein the birth tissue material composition comprises amniotic fluid and one or more morselized components of a placental organ selected from the group consisting of moselized chorionic membrane and morselized amniotic membrane.

2. The method of claim 1, wherein the step of administering human birth tissue material composition includes introducing a delivery device capable of delivering the human birth tissue material composition to at least one intervertebral space in need of treatment.

3. The method of claim 2, wherein the delivery device is introduced between a first vertebral body and second vertebral body in need of treatment.

4. The method of claim 2, further comprising the step of administering to the delivery device with the human birth tissue material composition after introduction of the device to the at least one intervertebral space in need of treatment.

5. The method of claim 2, wherein the delivery device retains, delivers, or both retains and delivers the effective amount of human birth tissue material composition.

6. The method of claim 2, wherein the delivery device is a vertebral body spacer, or formed from an umbilical cord, umbilical cord vein, or umbilical cord artery.

7. The method of claim 1, wherein the human birth tissue material composition is administered via at least one injection.

8. The method of claim 1, wherein the human birth tissue material composition further comprises autograft bone fragments or allograft bone fragments.

9. A method of generating intervertebral disc-like tissue in a human or vertebrate animal subject, said method comprising the step of
   administering to said subject a composition comprising an effective amount of a human birth tissue material composition to an intervertebral space within said subject,
   wherein the birth tissue material composition comprises amniotic fluid and one or more morselized components of a placental organ selected from the group consisting of moselized chorionic membrane and morselized amniotic membrane.

10. The method of claim 9, wherein the human birth tissue material composition is administered via at least one injection.

11. The method of claim 9, wherein the step of administering human birth tissue material composition includes introducing a delivery device to at least one intervertebral space in need of treatment.

12. The method of claim 11, wherein the delivery device is introduced between a first vertebral body and second vertebral body in need of treatment.

13. The method of claim 11, further comprising the step of administering to the delivery device with the human birth tissue material composition after introduction of the device to the at least one intervertebral space in need of treatment.

14. The method of claim 11, wherein the delivery device retains, delivers, or both retains and delivers the effective amount of human birth tissue material composition.

15. The method of claim 11, wherein the delivery device is a vertebral body spacer, or formed from an umbilical cord, umbilical cord vein, or umbilical cord artery.

16. The method of claim 9, wherein the human birth tissue material composition further comprises autograft bone fragments or allograft bone fragments.

* * * * *